US006254853B1

(12) United States Patent
Hendler et al.

(10) Patent No.: US 6,254,853 B1
(45) Date of Patent: Jul. 3, 2001

(54) WATER SOLUBLE PRO-DRUGS OF PROPOFOL

(75) Inventors: Sheldon S. Hendler, La Jolla, CA (US); Robert A. Sanchez, Riverton, UT (US); Jan Zielinski, San Diego, CA (US)

(73) Assignee: Vyrex Corporation, La Jolla, CA (US)

( * ) Notice: Subject to any disclaimer, the term of this patent is extended or adjusted under 35 U.S.C. 154(b) by 0 days.

(21) Appl. No.: 09/075,356

(22) Filed: May 8, 1998

(51) Int. Cl.[7] .................. A61K 9/12; A61K 9/10; A61K 9/14
(52) U.S. Cl. .................. 424/45; 424/489; 424/46; 424/423; 424/434; 424/449; 424/435; 424/450; 514/825; 514/826; 514/879; 514/903; 514/937
(58) Field of Search .................. 424/401, 45, 489; 514/143, 148, 772.6

(56) References Cited

U.S. PATENT DOCUMENTS

| | | |
|---|---|---|
| 5,308,874 | 5/1994 | Sanchez et al. . |
| 5,461,080 | 10/1995 | Sanchez et al. . |
| 5,478,857 | 12/1995 | Clemens et al. . |
| 5,496,537 * | 3/1996 | Henry ............... 424/45 |
| 5,607,691 * | 3/1997 | Hale et al. ............ 424/449 |
| 5,637,625 * | 6/1997 | Duncan Haynes ......... 514/731 |
| 5,714,520 | 2/1998 | Jones et al. . |

OTHER PUBLICATIONS

Castano, et al., Rev. Esp. Anestesiol. Reanim., 42(7):257–260 (1995).
M. Kuisma, et al., Epilepsia 36(12):1241–1243 (1995).
A. Borgeat, et al., Anesthesiology 80:642–656 (1994).
S. Lowson, et al., Brit. J. Anesthesia 64:59–63 (1990).
L. Aarts, et al., FEBS Let. 357(1):83–85 (1995).
Misacchia, et al., Pharmacol. Toxicol. 69:75–77 (1991).
A. Simonian, et al., Ann. Rev. Pharmacol. Toxicol. 36:83 (1996).
Helveston, et al., Clinical Neuropharmacology 19(3):271 (1996).
Jenner, Pathologie Biologie 44(1):57 (1996).
Good, et al., Am. J. Pathol. 149(1):21 (1996).
Borlongan, et al., Journal of the Florida Medical Association, 83(5):335 (1996).
M. Cudkowicz, et al., Glutathione in the Nervous System, Ch. 16, Shaw, Ed. (1998).
D. Hooper, et al., Proc. Natl. Acad. Sci. USA 95:675–680 (1998).
Castellani, et al., Brain Research, 696(1–2):268 (1995).
Beal, Annals of Neurology 38(3):357 (1995).
Briggs, et al., Anesthesia 37:1099 (1982).
McHugh, et al., Can J. Anaesth. 42(9):801–804 (1995).
Bielen, et al., Anesth. Analg. 82(5): 920–924 (1996).
R. Chinery, et al., Natural Medicine 3:1233–1241 (1997).
P. Eikelenboom, et al., TiPS 15:447–450 (1994).
L.A. Belova, Biochemistry (Russia) 62(6):563–570 (1997).
I.L. Chapple, J. Clinical Peridontol (Denmark) 24(5):287–296 (1997).
S.R. Maxwell, Drugs (New Zealand) 49(3):345–361 (1995).
E.M. Conner, Nutrition 12(4):274–277 (1996).
E. Ignatowicz, Pol J. Pharmacol (Poland) 46(3):103–114 (1994).
Trapani et al., "Water–soluble salts of aminoacid esters of the anaesthetic agent Propofol," International Journal of Pharmaceuticals, 175:195–204 (1998(.*

* cited by examiner

Primary Examiner—James M. Spear
Assistant Examiner—S. Howard
(74) Attorney, Agent, or Firm—Townsend and Townsend and Crew LLP

(57) ABSTRACT

This invention provides esters of propofol (2,6,-diisoprophenol). The propofol esters are soluble in water and metabolize rapidly to propofol in the body. The propofol esters are useful as pro-drugs for the same indications as propofol. This invention also provides methods of treating neurodegenerative diseases by administering as effective amount of propofol.

48 Claims, No Drawings

WATER SOLUBLE PRO-DRUGS OF PROPOFOL

BACKGROUND OF THE INVENTION

This invention relates to the field of pharmaceuticals. More specifically, this invention relates to pro-drugs of propofol that are water soluble and non-toxic.

Propofol (2,6-diisopropylphenol) is a low molecular weight phenol that is widely used as an intravenous sedative-hypnotic agent in the induction and maintenance of anesthesia or sedation in humans and animals. Among its advantages as an anesthetic are rapid onset of anesthesia, rapid clearance, and minimal side effects.

Propofol has a broad range of biological and medical applications. For example, it has been reported to be an anti-emetic (Castano et al., *Rev. Esp. Anestesiol. Reanim.* 42(7):257–60 (1995)), an anti-epileptic (Kuisma M. et al. *Epilepsia* 36(12):1241–1243 (1995)) and an anti-pruritic. (Borgeat, A. et al., *Anesthesiology* 80:642–56 (1994); Lawson, S. et al., *Brit. J. Anesthesia* 64:59–63 (1990).)

Propofol also has significant application as an antioxidant. (Sanchez et al., U.S. Pat. No. 5,308,874; Sanchez et al., U.S. Pat. No. 5,461,080; and Aarts L. et al. *FEBS Let.* 357(1):83-5 (1995).) In fact, it has been proposed that propofol can replace α-tocopherol as antioxidant. (Aarts, supra.) Oxidative processes in living materials can result in significant damage. For example, oxidizing agents in the environment, such as smoke or ozone, are inhaled and cause oxidative stress to tissues of the respiratory system. Exposure to sunlight causes damage to skin as a result of chain reactions which originate when the ultraviolet light promotes the production of free radicals, such as superoxide and hydroxyl, within the tissue surface. Other forms of energetic radiation can have the same effect.

Propofol also has been shown to inhibit lipid peroxidation. (Misacchia et al., *Pharmacol. Toxicol.* (1991) 69:75–77.)

Oxidation also is a component of inflammation. For example, cyclooxygenase oxidizes arachidonic acid into prostaglandins which act as inflammatory mediators. Therefore, inhibiting oxidation is useful in the treatment of conditions with an inflammatory component. In addition, oxidative damage is also caused by other inflammation mediators such as tumor necrosis factor (TNF) and IL-1.

By inhibiting oxidation in tissues of the respiratory tract, propofol is useful in the prophylactic and therapeutic treatment of various pathologic respiratory conditions having an inflammatory component. These include, for example, acid aspiration, adult/infant respiratory distress syndrome, airway obstructive disease, asthma, bronchiolitis, bronchopulmonary dysplasia, cancer, chronic obstructive pulmonary disease ("COPD"), cystic fibrosis, emphysema, HIV-associated lung disease, idiopathic pulmonary fibrosis, immune-complex-mediated lung injury, exposure to an oxidizing agent, ischemia-reperfusion injury, mineral dust pneumoconiosis, drug-induced lung disease and silo-filler's disease.

There is an extensive accumulation of evidence that either the pathogenesis or the subsequent damage pathways in various neurodegenerative diseases involve reactive oxygen species, and are therefore amenable to treatment with anti-oxidants. (A review of this subject is given by Simonian A. and Coyle J. T., "Oxidative Stress in Neurodegenerative Diseases", in *Ann. Rev. Pharmacol. Toxicol.* 36:83 (1996).) Examples of specific neurodegenerative diseases where oxidative damage may play a role include Friedrich's disease (Helveston et al., *Clinical Neuropharnacology* 19(3):271 (1996)), Parkinson's disease (Jenner, *Pathologie Biologie* 44(1):57 (1996)), Alzheimer's disease (Good et al., *Am. J. Pathol.* 149(1):21 (1996)), Huntington's disease (Borlongan et al., *Journal of the Florida Medical Association* 83(5):335 (1996)), amyotrophic lateral sclerosis (ALS) (Cudkowicz, M. et al. "Free-Radical Toxicity in Amyotrophic Lateral Sclerosis," Ch. 16 in *Glutathione in the Nervous System*, Shaw, Ed. (1998); multiple sclerosis (MS) (Hooper, D. et al. "Uric acid, a natural scavenger of peroxynitrite, in experimental allergic encephalomyelitis and multiple sclerosis," *Proc. Natl. Acad. Sci. USA* 95:675–680 (1998)); Pick disease (Castellani et al., *Brain Research* 696(1–2):268 (1995)) and aging itself (Beal, *Annals of Neurology* 38(3):357 (1995).)

Similarly, the incidence of spinal cord injury in the United States is approximately 10,000 new cases per year. The human and financial costs of such injuries are devastating and therapies for treatment of these injuries are urgently needed. There is an accumulation of evidence that the pathogenesis of spinal cord injury, as well as injury to the brain, also involves reactive oxygen species and is therefore amenable to treatment with antioxidants (Castano et al., *Rev. Esp. Anestesiol. Reanim.* 42(7):257–60 (1995)). Alpha-tocopherol (vitamin E), a well known antioxidant, has been shown to decrease post-traumatic spinal cord ischemia and to enhance chronic neurological recovery. However, vitamin E is taken up into the central nervous system very slowly, making it an impractical agent for the treatment of acute neural injury.

A disadvantage to the use of propofol is that it is almost completely insoluble in water. Therefore, before it can be used for intravenous applications, such as anesthesia, it must be specially formulated in aqueous media using solubilizers or emulsifiers. The early developmental studies with intravenous propofol were performed with clear formulations containing the solubilizer Cremophor EL®. Later developmental studies and the current commercial products use an oil-in-water emulsion in which the emulsifier is the lecithin mixture Intralipid®. The commercial products are sold under various names including Diprivan®, Disoprofol®, Disoprivan®, and Rapinovet®.

Formulations that contain solubilizers or emulsifiers have been fraught with problems. Formulations containing the solubilizer Cremophor EL® have been reported to cause allergic complications (Briggs et al., *Anesthesis* 37:1099 (1982)). Stable emulsions are technically difficult to prepare and are consequently more expensive. Microbial growth has sometimes been observed in such emulsions and is believed to be supported by the emulsifier components (McHugh et al., *Can. J. Anaesth.* 42(9):801–4 (1995)).

Other investigators have sought to overcome the problem of water insolubility by incorporating the propofol within a water-soluble carrier such as a cyclodextrin. Such a molecular complex allows delivery of propofol in a clear water solution and the eventual release of propofol in vivo. Unfortunately, the cyclodextrin complex produced cardiovascular complications in vivo, discouraging further study (Bielen et al., *Anesth. Analg.* 82(5):920–4 (1996)).

Until now, there has been no pharmaceutical preparation of propofol formulated to deliver its beneficial effects without harmful side effects. Thus, the need exists for a water-soluble, stable, non-toxic pharmaceutical composition which is readily converted to propofol in vivo without the need for additives, solubilizers or emulsifiers.

SUMMARY OF THE INVENTION

This invention provides novel esters of propofol (2,6-diisopropylphenol) that are highly soluble in water and that metabolize rapidly into propofol. More specifically, this invention provides propofol hemisuccinate, propofol hemiglutarate, propofol hemiadipate, mono(propofol) phosphate, and di(propofol) phosphate. The esters of the present invention are at least one order of magnitude more soluble in water than propofol. The monophosphate and hemisuccinate esters are the most soluble.

The pro-drugs of this invention have little or no direct antioxidant activity, as a consequence of blockage of the phenolic group of the propofol molecule. In an in vivo environment, biological enzymes cause the hydrolysis of the pro-drugs, resulting in the release of free propofol, a potent antioxidant. Therefore the pro-drugs of this invention, when used in biological environments, possess all of the therapeutic applications that have been demonstrated for propofol.

These compositions offer advantages over propofol. First, the esters of propofol of this invention readily hydrolyze to propofol in vivo. Accordingly, they are useful as pro-drugs of propofol. Second, they are non-toxic. Accordingly, they have a high therapeutic-to-toxicity index. Third, they have a much higher water-solubility than propofol. Thus, they offer a safer means of administration than the current commercially available oil-in-water or cyclodextrin formulations. Fourth, they are more stable to oxidation than propofol because they protect the phenolic function from oxidation during formulation and storage. Phenols are well known to darken and decompose in the presence of air. Therefore, the esters of propofol of this invention offer all the therapeutic effects of propofol while avoiding the necessity of adding potentially harmful solubilizing or emulsifying agents.

A soluble pro-drug facilitates formulation and administration of the drug. How fast the drug is released in vivo by hydrolysis is a function of the structure of the pro-drug; but it is also influenced by the carrier, the route of administration, and the tissues in which the pro-drug is located.

The pro-drugs of this invention act in vivo as anti-oxidant and anti-inflammatory agents. They are useful in the treatment of oxidative tissue damage, diseases having an inflammatory component and cancer, in particular when co-administered with a chemotherapeutic agent. Propofol and the pro-drugs of this invention also have uses as hypnotic agents, anti-convulsives, anti-pruritics, and anti-emetics.

In one aspect this invention provides a propofol pro-drug of the formula:

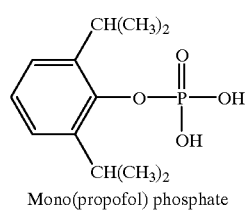
Mono(propofol) phosphate (1)

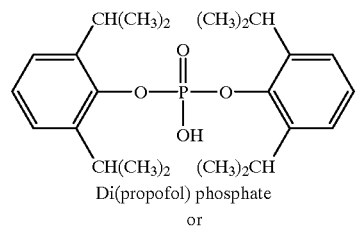
Di(propofol) phosphate (2)

or

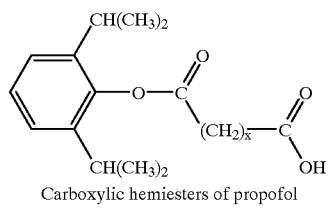
Carboxylic hemiesters of propofol (3)

wherein X is 2, 3 or 4, or a pharmaceutically acceptable salt of any of the foregoing.

In another aspect this invention provides a pharmaceutical composition comprising a pharmaceutically acceptable carrier and a pharmacologically effective amount of a propofol pro-drug of this invention.

In another aspect this invention provides a method for inhibiting oxidation of biological material comprising contacting the material with an effective amount of a propofol pro-drug of this invention.

In another aspect this invention provides a method for the treatment of a pathologic condition having an inflammatory component in a subject comprising administering to the subject a pharmacologically effective amount of a propofol pro-drug of this invention.

In another aspect this invention provides a method for the treatment of a pathologic condition of the nervous system having an inflammatory component in a subject comprising administering to the subject a pharmacologically effective amount of propofol or a propofol pro-drug of this invention.

In another aspect this invention provides a method for the treatment of a pathologic respiratory condition in a subject comprising administering to the subject a pharmacologically effective amount of a propofol pro-drug of this invention.

In another aspect this invention provides a method for inducing anaesthesia in a subject comprising administering to the subject a pharmacologically effective amount of a propofol pro-drug of this invention.

In another aspect this invention provides a method for inhibiting nausea and vomiting in a subject comprising administering to the subject a pharmacologically effective amount of a propofol pro-drug of this invention.

In another aspect this invention provides a method for the treatment of epileptic or convulsive disorders in a subject comprising administering to the subject a pharmacologically effective amount of a propofol pro-drug of this invention.

In another aspect this invention provides a method for the treatment of pruritis in a subject in a subject comprising administering to the subject a pharmacologically effective amount of a propofol pro-drug of this invention.

In another aspect this invention provides a method for the treatment of a cancer in a subject comprising administering to the subject a chemotherapeutic agent and a pharmacologically effective amount of a propofol pro-drug of this invention.

In another aspect this invention provides a method for the treatment of a subject undergoing treatment with a chemotherapeutic agent having activity as an oxidizing agent comprising the step of administering a pharmacologically effective amount a propofol pro-drug of this invention to the subject.

In another aspect, this invention provides the use of a water-soluble propofol pro-drug of this invention in the manufacture of a medicament for the treatment of a pathological condition having an inflammatory component.

DETAILED DESCRIPTION OF THE INVENTION

I. Water Soluble Esters of Propofol

Propofol is rendered water soluble by the linking of hydrophilic groups to the molecule. Such covalent derivatization of propofol is possible only on the phenolic —OH group, which is flanked on both sides by bulky isopropyl groups. The —OH group is therefore spatially crowded ("sterically hindered") and would be expected to be resistant to the substitution of the hydrogen with a bulkier substituent such as an acyl group or a phosphoryl group.

The synthesis of esters however was successfully achieved by the use activated diacids (as halides or anhydrides), and by simultaneous use of either catalysis by tertiary amines, or activation of the phenol by ionization of the phenolic proton.

Preferred compounds in accordance with the present invention are those having the following formulae:

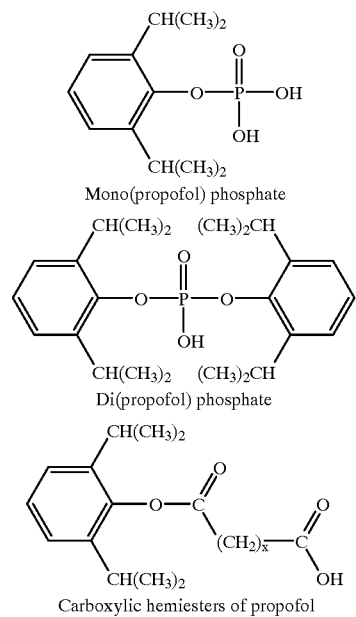

Mono(propofol) phosphate

Di(propofol) phosphate

Carboxylic hemiesters of propofol

In the above structure for carboxylic hemiesters of propofol, X=2 is the hemisuccinate ester of propofol; X=3 is the hemiglutarate ester of propofol; and X=4 is the hemiadipate ester of propofol.

Preferred compounds of the present invention also include pharmaceutically acceptable salts of the compounds of the above formulae. A "pharmaceutically acceptable salt" is a salt that can be formulated into a compound for pharmaceutical use including, e.g., metal salts (sodium, potassium, magnesium, calcium, etc.) and salts of ammonia or organic amines.

II. Prophylactic and Therapeutic Treatments

Propofol and the pro-drugs of this invention are useful for the prophylactic and therapeutic treatment of subjects as described herein. A "subject" of treatment is an animal, such as a mammal, including a human. Non-human animals subject to treatment include, for example, fish, birds, and mammals such as cows, sheep, pigs, horses, dogs and cats. "Treatment" refers to prophylactic or therapeutic treatment. A "prophylactic" treatment is a treatment administered to a subject who does not exhibit signs of a disease or exhibits only early signs for the purpose of decreasing the risk of developing pathology. Thus, administration of the compound to a person who is exposed to an oxidant has a prophylactic effect in inhibiting oxidative tissue damage. A "therapeutic" treatment is a treatment administered to a subject who exhibits signs of pathology for the purpose of diminishing or eliminating those signs.

III. Use as an Anti-Oxidant and Anti-Inflammatory

Oxidation is a source of serious damage to biological molecules, including nucleic acids, proteins, lipids and carbohydrates. It is consequently also a source of damage to biological structures composed of such molecules, e.g., cell membranes, tissues and vasculature. The source of oxidants can be external to an organism, for example from the environment, or internal, as a result of the natural production of free radicals by, for example, the mitochondria, or as a result of the inflammatory response.

Propofol and the pro-drugs of this invention are useful in methods of inhibiting oxidation in biological materials. The methods involve contacting the biological material with an effective amount of the compound. In the therapeutic methods of this invention, a pharmacologically effective amount of the compound is administered to a subject suffering from a pathological condition responsive to inhibition of oxidation. In the prophylactic methods of this invention a pharmaceutically effective amount of the compound is administered to a subject at risk of developing a disease as a result of exposure to oxidative stress.

"Biological material" refers to cells, tissues, organs, extracts, homogenates, fluids or cultures both in vitro and in vivo. In one aspect, this invention provides methods of inhibiting oxidation of biological material in a subject by administering to the subject an amount of the compound effective to inhibit the oxidation. In another aspect, this invention provides methods of inhibiting oxidation to biological material in vitro by contacting the material with an amount of the compound effective to inhibit the oxidation.

Inflammation is characterized at the cellular level by the production of inflammatory mediators, such as cytokines (e.g., TNF-α, IL-1). The production of cytokines involves an oxidation step that is cyclooxygenase dependent. Inflammation at the cellular level is also characterized by the production of other inflammatory mediators, such as eicosanoids (e.g., prostaglandins, prostacyclins, thromboxanes and leukiotrienes). The production of prostaglandins, prostacyclins and thromboxanes all involve an oxidation step that is cyclooxygenase dependent. At the tissue level, inflammation is characterized by invasion of leukocytes, especially neutrophils, macrophages and lymphocytes. Therefore, it appears that most or all inflammation involves an oxidative component. Because they inhibit oxidation, propofol and the pro-drugs of this invention are useful in the treatment or prevention of conditions having an inflammatory component. A pharmacologically effective amount of the compound is administered to a subject suffering from, or at risk of suffering from, a pathological condition which can be improved by inhibiting inflammation. In general, an effective dose is about 100 mg to about 1 gm taken orally per day.

A. Arthritis

Arthritis is an inflammatory condition. Accordingly, propofol and the pro-drugs of this invention are useful in treating arthritis, both rheumatoid arthritis and osteoarthritis. The compounds preferably are delivered orally or transdermally for this purpose. A pharmacologically effective amount of the agent taken orally is about 50 mg to about 2 g. daily.

B. Respiratory Disorders

Because they can be administered to the respiratory system via inhalation, propofol and the pro-drugs of this invention are useful in the treatment of respiratory disorders having an inflammatory component. The anti-oxidant compounds of this invention inhibit oxidation and its subsequent damage that result in or accompany such disorders. Accordingly, they are useful in the prophylactic or therapeutic treatment of respiratory disorders that involve an inflammatory component or that result from exposure to oxidizing agents.

Respiratory diseases that can be treated with these compounds include acid aspiration, adult/infant respiratory distress syndrome, airway obstructive disease, asthma, bronchiolitis, bronchopulmonary dysplasia, cancer, chronic obstructive pulmonary disease ("COPD"), cystic fibrosis, emphysema, HIV-associated lung disease, idiopathic pulmonary fibrosis, immune-complex-mediated lung injury, exposure to an oxidizing agent, ischemia-reperfusion injury, mineral dust pneumoconiosis, drug-induced lung disease and silo-filler's disease.

Exposure to oxidizing agents such as dust, ozone, hyperoxia, air pollution, nitric oxide, nitrogen dioxide, sulfur dioxide, tobacco smoke, diesel exhaust or other combustion byproducts also can be treated with propofol or the pro-drugs of this invention.

In the treatment of respiratory conditions, the compound is preferably delivered by inhalation. The compound can be delivered as an aerosol, mist or powder. An effective amount for delivery by inhalation is about 0.1 mg to 10 mg per inhalation, several times daily. The compound also can be delivered orally in amounts of about 50 mg to about 2 g daily.

C. Disorders Of The Central Nervous System

Propofol and the pro-drugs of this invention are particularly useful in inhibiting oxidation and its resultant damage in disorders of the central nervous system that involve an inflammatory component. This results both from their anti-oxidant properties and because, once introduced into the system, they rapidly equilibrate in the various compartments, including the central nervous system. Also, lipophilicity and small size of propofol favor penetration into the nervous system and brain, which is why it can function as an anesthetic. Rapid and significant penetration is not a feature of many other antioxidants, such as alpha-tocopherol (Vitamin E) and ascorbic acid (vitamin C). Thus, these compounds are useful in the treatment of nervous system disorders.

Neurodegenerative conditions of the nervous system include Friedrich's disease, Parkinson's disease, Alzheimer's disease, Huntington's disease, Pick disease, amyotrophic lateral sclerosis and multiple sclerosis.

Propofol and the pro-drugs of this invention also are useful in treating trauma to the central nervous system. These include, for example, skull fracture and its resulting edema, concussion, contusion, brain hemorrhages, shearing lesions, subdural and epidural hematoma, and spinal cord injury (e.g., mechanical injury due to compression or flexion of the spinal cord).

In the treatment of traumatic conditions of the central nervous system, the compound preferably is administered parenterally, such as by intravenous injection or injection directly into the central nervous system (i.e., intrathecally (IT) or into the brain). A pharmacologically effective amount of the compound is about 25 mg to about 500 mg IV or IM and about 5 mg to about 100 mg IT. The treatment of chronic neurodegenerative disease is best effected via oral administration of an effective amount of the compound, preferably 50 mg to 2 g daily.

D. Cardiovascular Disorders

Propofol and the pro-drugs of this invention are useful in preventing/treating cardiovascular disease, including but not limited to ischemia-reperfusion dysfunction, atherosclerosis and restenosis following angioplasty. Oral, enteral or intravenous administration is useful for this purpose.

IV. Treatment of Cancer

It is now recognized that co-administration of anti-oxidants improves the outcome of chemotherapy in subjects with cancer. (R. Chinery et al. *Nature Medicine* 3:1233–1241 (1997).) As an example, co-administration of pyrrolidine dithiocarbamate (PDTC) or vitamin E with 5-fluorouracil or doxorubicin inhibited the growth of colorectal cancer tumors in mice.

Propofol and the pro-drugs of this invention, which function as anti-oxidants, are useful in the treatment of cancer or as adjuvants in the treatment of cancer. Co-administered with chemotherapeutic agents, they enhance cytotoxicity, thereby inhibiting the growth of tumors. In addition, they also inhibit oxidative damage that generally accompanies use of anticancer agents. Methods of treating cancer involve administering a pharmacologically effective amount of the compound to a subject prior to, during or after chemotherapy. The compounds are useful in the treatment of any cancer. However, they are particularly effective in the treatment of colorectal cancer and lung cancer. The compounds also are effective with chemotherapeutic agents that act by all known modes of action.

The compounds preferably are delivered as a pharmaceutical composition in the form of an intravenous or intramuscular solution. However, other modes of delivery, such as enteral administration, also are useful. An effective amount of the agent is about 50 mg to about 2 g delivered daily over the course of the chemotherapy regimen.

V. Use to Prevent/Ameliorate Chemotherapeutic Toxicity

Propofol and the pro-drugs of this invention can be used to prevent or ameliorate the effects of chemotherapeutic agents that have oxidative damage as a significant side effect, e.g., bleomycin, doxorubicin and cisplatin. The methods involve administering a pharmacologically effective amount a compound of the invention to a subject undergoing chemotherapy treatment.

VI. Use as a Hypnotic Agent and as a Sedative

Propofol and the pro-drugs of this invention are useful as hypnotic agents for the same indications as propofol. These include inducing and/or maintaining general anaesthesia and use as a sedative. The compound is administered in an amount effective to induce hypnosis.

For use as a general anaesthetic, the compounds are preferably administered as an intravenous solution. However, they also can be administered by inhalation.

Compositions of propofol are presently administered as an injectable oil-in-water emulsion, due to the very low water solubility of propofol. The pro-drugs of this invention can be formulated in the same manner. However, the pro-drugs of this invention are more highly water soluble than propofol. Accordingly, they can be delivered as an aqueous solution or with significantly less emulsifiers or solubilizers.

For use as a sedative (e.g., for the treatment of anxiety conditions), the compounds are preferably and effectively administered orally in amounts of about 10 mg to 2 g daily. However, they can also be administered by inhalation, intravenously or intramuscularly.

The pro-drugs of this invention are administered in similar amounts and in the same schedule as injectable emulsions of propofol (e.g., DIPRIVAN®). Dosage level of propofol for producing general anesthesia, both induction (for example about 2.0 to about 2.5 mg/kg for an adult) and maintenance (for example, about 4 to about 12 mg/kg/hr) and for producing a sedative effect (for example, about 0.3 to about 4.5 mg/kg/hr) may be derived from the very substantial literature on propofol. The actual dosages of the propofol pro-drugs, on a weight basis, will in many cases be higher than for propofol itself because (a) the molecular weights of the pro-drugs are higher and (b) release of propofol from the pro-drug occurs at a finite rate. Furthermore, the anesthetist and/or physician would modify the dose to achieve the desired effect in any particular patient, in accordance with normal skill in the art.

VII. Use as a Anti-Emetic

Propofol and the pro-drugs of this invention are useful as anti-emetics. Their administration is indicated in subjects at risk of vomiting or who feel nauseous. As an example, the compounds are usefully co-administered to subjects who are receiving treatments that induce nausea, such as various chemotherapy agents and surgical procedures. Accordingly, this invention provides methods for inhibiting nausea and vomiting by administering the compound to a subject in an amount effective to inhibit nausea and vomiting.

In the prophylactic or therapeutic treatment of nausea or vomiting, the compounds preferably are delivered orally in a pharmaceutical composition. Accordingly, solid or liquid carriers are appropriate delivery vehicles. However, parenteral routes of administration, such as inhalation or injection, also are useful as well as topical and transdermal administration.

For use as an anti-emetic, the compounds are effectively administered in amounts of about 50 mg to about 2 g.

VIII. Use as a Anti-convulsive

Propofol and the pro-drugs of this invention are useful as anti-convulsives to prevent or relieve seizures including, e.g., epileptic seizures. This invention provides methods for inhibiting convulsions comprising administering to a subject an amount of the compound effective to inhibit convulsions.

In the prophylactic or therapeutic treatment of seizures the compounds preferably are delivered orally or parenterally.

For use as an anti-convulsive, the compounds are effectively administered in amounts of about 50 mg to about 2 g daily.

IX. Use as an Anti-pruritic

Propofol and the pro-drugs of this invention are useful as anti-pruritics to prevent or relieve itching. This invention provides methods of inhibiting itching comprising administering the compound to a subject in an amount effective to inhibit itching. The compounds can treat both external and internal itching. The source of itching can be any disease or exposure to a pruritic agent, such as poison ivy.

In the prophylactic or therapeutic treatment of itching, the compounds preferably are delivered topically in a pharmaceutical composition. Various creams and ointments are appropriate delivery vehicles.

For use as an anti-pruritic, the compounds are effectively administered in amounts of about 50 mg to about 2 g daily or rubbed into the skin at about 0.01 to about 5 mg/cm$^2$. Sub-sedative dose for pruritus may be achieved at between about one-quarter and about one-tenth the anesthetic dose.

X. Pharmaceutical Compositions and Modes of Delivery

Propofol and the pro-drugs of this invention preferably are delivered as pharmaceutical compositions. "Pharmaceutical composition" refers to a composition suitable for pharmaceutical use in a subject. The pharmaceutical compositions of this invention comprise a pharmacologically effective amount of a compound of the invention and a pharmaceutically acceptable carrier. "Pharmacologically effective amount" refers to that amount of the compound effective to produce the intended pharmacological result, e.g., inhibit oxidation, induce anaesthesia, inhibit vomiting, inhibit convulsions, inhibit itching, or inhibit inflammation. "Pharmaceutically acceptable carrier" refers to any of the standard pharmaceutical carriers, buffers, and excipients, such as a phosphate buffered saline solution, aqueous solutions of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent.

The compounds of the invention can be formulated for administration in a variety of ways. Typical routes of administration include both enteral and parenteral. These include, without limitation, subcutaneous, intramuscular, intravenous, intraperitoneal, intramedullary, intrapericardiac, intrabursal, oral, sublingual, ocular, nasal, topical, transdermal, transmucosal, or anal. The mode of administration can be, e.g., via swallowing, inhalation, injection or topical application to a surface (e.g., eyes, mucus membrane, skin).

Particular formulations typically are appropriate for specific modes of administration. Various contemplated formulations include, for example, aqueous solutions, solid formulations, aerosol formulations and transdermal formulations.

A. Aqueous Solutions for Enteral, Parenteral Or Transmucosal Administration

Examples of aqueous solutions include, for example, water, saline, phosphate buffered saline, Hank's solution, Ringer's solution, dextrose/saline, glucose solutions and the like. The compositions can contain pharmaceutically acceptable auxiliary substances as required to approximate physiological conditions or to improve stability, appearance or ease of administration, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection and, in particular, for intravenous injection. Intravenous injection is a particularly appropriate means of delivery for using the compound as a hypnotic agent. The intravenous solution can include detergents and emulsifiers such as lipids. Aqueous solutions also are useful for enteral administration as tonics and administration to mucous or other membranes as, e.g., nose or eye drops. The composition can contain the compound in an amount of about 1 mg/ml to 100 mg/ml, more preferably about 10 mg/ml.

B. Solid and Other Non-Aqueous Compositions For Enteral Or Transdermal Delivery

Solid compositions are appropriate for enteral administration. They can be formulated in the form of, e.g., pills, tablets, powders or capsules. For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10%–95% of active ingredient.

The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, maltose, rice, flour, chalk, silica gel, magnesium stearate, sodium stearate, glycerol monostearate, sodium chloride, dried skim milk, glycerol, propylene glycol, water, ethanol, and the like.

A unit dosage form, such as a tablet, can have about 10 mg to about 2 g of the compound.

Solid compositions are particularly useful for using the compound as an anti-emetic.

C. Topical Administration For Transdermal Or Transmucosal Delivery

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one embodiment, the transdermal delivery agent can be DMSO.

Transdermal delivery systems can include, e.g., patches.

Topical administration is particularly useful for use of the compound as an anti-pruritic or in the treatment of wounds with an inflammatory component such as burns, rashes and sunburns. However, sustained administration can deliver the compound for use as an anti-oxidant and anti-inflammatory agent internally.

D. Delivery By Inhalation

For inhalation, the compound is preferably administered in the form of an aerosol, liquid or solid. For aerosol administration, the compound preferably is supplied in finely divided form along with a surfactant and propellant. A surfactant may be required if the agent is immiscible in the propellant.

The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides, can be employed. The surfactant can constitute 0.1%–20% by weight of the composition, preferably 0.25%–5%.

The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the agent as a solution or as finely divided particles and surfactant. The ingredients are thus maintained at an elevated pressure until released by action of the valve.

A nebulizer or aerosolizer device for administering compounds typically delivers a dose of about concentration of between about 1 and 50 mg per inhalation.

Delivery by inhalation is particularly effective for delivery to respiratory tissues for the treatment of respiratory conditions including an inflammatory component. Delivery of large doses by respiration also can induce sedation or anaesthesia. Anesthesia may be achieved by means of continuous inhalation such as occurs with propofol, ether, or other conventional anesthetics. Induction may occur at doses between about 200 mg and about 400 mg inhaled over a period of a few minutes (e.g., about 5 to about 15 minutes). Sedation may be maintained thereafter at a dose of about 200 mg to about 400 mg per hour for as long as is needed.

E. Other Formulations

In preparing pharmaceutical compositions of the present invention, it can be desirable to modify the complexes of the present invention to alter their pharmacokinetics and biodistribution. For a general discussion of pharmacokinetics, See, *Remington's Phamaceutical Sciences*, supra, Chapters 37–39. A number of methods for altering pharmacokinetics and biodistribution are known to one of ordinary skill in the art. Examples of such methods include protection of the complexes in vesicles composed of substances such as proteins, lipids (for example, liposomes), carbohydrates, or synthetic polymers.

F. Administration

Single or multiple administrations of the compositions can be carried out with dose levels and pattern being selected by the treating physician. In any event, the pharmaceutical formulations should provide a quantity of a compound sufficient to treat the patient effectively.

The total effective amount of a compound of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a compound of the present invention required to obtain an effective dose in a subject depends on many factors including the age and general health of the subject, the route of administration, the number of treatments to be administered and the judgment of the prescribing physician. In view of these factors, the skilled artisan would adjust the dose so as to provide an effective dose for a particular use.

The following examples are offered by way of illustration, not by way of limitation.

EXAMPLES

Example 1
Synthesis of propofol hemnisuccinate

Succinic anhydride (14 g, 140 mmol) and dimethylaminopyridine (0.02 g, 0.16 mmol) were added to a solution of 2,6-diisopropylphenol (20.8 ml, 112 mmol) in triethylamine (50 ml) under nitrogen. After 16 hr at room temperature, solvents were removed under vacuum. The residue was dissolved in water and added to an iced solution of dilute hydrochloric acid. The precipitated product was filtered and recrystallized from ethanol-water to yield 25.0 g (80.2% yield) of 2,6-diisopropylphenyl hydrogen succinate (propofol hemisuccinate), mp 101–102° C.

High resolution nuclear magnetic resonance spectra are fully consistent with structure: $^1$H-NMR (500 MHz, CDCl$_3$) δL 1.207(d, 12H, J=6.9 Hz, di-I-Pr), 2.856(t, 2H, J=6.7 Hz, C3'—H$_2$), 2.940(q, 2H, J=6–9 HZ, C$_7$H, C$_8$—H), 2.961 (t, 2H, J=6.7 Hz, C$_2$—H$_2$), 7.173(d, 2H, J=7.8 HZ, C$_3$H, C$_5$—H), 7.224(d, 1H, J=7.8 Hz, C$_4$H $^{31}$P-NMR (500 Mhz, CDCl$_3$) ι: −9.6994 $^{13}$C-NMR (500 MHZ, CDCl$_3$) δ: 22.929 (C-3'), 23.916(C-2'), 27.639(C-9, C-10, C-11, C-12), 28.815 (CO7), 29.085(C-8), 124.122(C-3, C-5), 126.805(C-4), 140.456(C-2, C-6), 145.633(C-1), 171.000(C-1'), 178.838 (C-4')

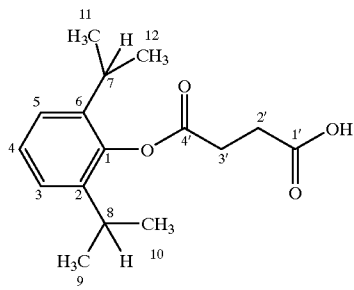

Example 2
Synthesis of propofol hemiadipate Triethylamine (6.26 ml, 45 mmol) and 4-dimethylaminopyridine (50 mg, 0.4 mmol) in methylene chloride (30 ml) were added to a solution of 2,6-diisopropylphenol (5.2 ml, 28 mmol) and adipoyl chloride (4.4 ml, 30 mmol) in methylene chloride (50) at 0° C. The mixture was allowed to reach room temperature and stirred at that temperature for 2 hr. Water (50 ml) was added, and the two-phase mixture was stirred for 1 hr. The organic phase was washed with 3% aqueous HCl and then dried. Solvents were removed under vacuum, and the oily residue was chromatogrammed on a silica gel column using chloroform-methanol (10:0.1) and then chloroform-methanol-acetic acid (10:0.1:0.01). The fractions containing the ester were pooled and evaporated under vacuum to yield 3.4 g (40% yield) of 2,6-diisopropylphenol hydrogen adipate (propofol hemiadipate) as an oil.

The $^1$H-NMR and $^{13}$C-NMR spectra were very similar to those of the hemisuccinate ester (example 1) and fully consistent with structure. Splitting of signals however show that the compound exists as a mixture of rotamers, most likely the result of hindered rotation about the acyl-phenoxyl linkage.

Example 3
Synthesis of propofol hemisuccinate sodium salt

A solution of propofol hemisuccinate (1.0 g, 3.6 mmol) in 10 ml of ethanol was neutralized with 3.6 ml of 1.0 N NaOH. The solvents were removed under vacuum, and water was fully removed by further addition and evaporation of acetonitrile under vacuum. The crystalline product was washed with acetonitrile and dried under high vacuum at 60° C. The yield of propofol hemisuccinate sodium salt was 0.97 g (90%).

The high resolution proton magnetic resonance spectrum and fast atom bombardment mass spectrum are fully consistent with structure: $^1$H-NMR (500 MHz, D$_2$O)δ: 1.13(d, 12H, J=6.8 Hz, di-i-Pr), 2.622(t, 2H, J=6.7 Hz, C$_3$'—H2), 2.919(q, 2H, J=6.8 Hz, C$_7$H, C$_8$H), 2.937(t, 2H, J=6.7 Hz, C$_2$—H2), 7.275(m, 3H, C$_3$H, C$_4$H, C$_5$H) FAB-MS: [M+H]$^+$301.1410 M/Z, calculated for C$_{16}$H$_{21}$O$_4$Na+H formula 301.1417

Example 4
Synthesis of mono(propofol) phosphate disodium salt

Butyllithium (2.24 ml of 2.5 M solution in hexanes; 5.6 mmol) was added dropwise to propofol (1.0 g, 5–6 mmol) in 10 ml of ether at −30° C. under nitrogen. The solution was stirred at −30° C. for 30 in then allowed to warm to room temperature. This solution was then added dropwise to a solution of phosphorus oxychloride (0.918 g, 6.0 mmol) in 10 ml of ether at −30° C. The solution was allowed to warm to room temperature, then water (5 ml) was added and stirring was continued for 1 hr. Sodium hydroxide (35 ml of 1 M) and 30 ml of hexanes was added. The aqueous phase was washed with hexanes, then acidified with HCl to pH 3 and extracted with ether. After evaporation of the solvents, the oily residue was dissolved in ethanol and neutralized to pH 7.4 with 1 M NaOH. After removal of the solvents in vacuo, the residue was suspended in acetonitrile, and the solid product was collected and dried. The yield of mono (propofol) phosphate disodium salt was 1.1 g (65%).

The high resolution nuclear magnetic resonance spectra (proton, carbon and phosphorus) in water, and the fast atom bombardment mass spectrum are fully consistent with structure. The magnetic resonance spectra show the presence of two rotamers in a population ratio of 7:1: $^1$H-NMR (500 MHz, D$_2$O)δ: 1.184 and 1.205 (d,d, 12H, J=6.8 Hz, di-i-Pr), 3.519 and 3.619 (m,m, 2H, C$_7$—H, C$_8$—H), 7.198 (m, 3H, C$_3$—H, C$_4$—H, C$_5$—H) $^{13}$C-NMR (500 MHz, D$_2$O)δ: 21.986 and 22.083 (C-9, C-10, C-11, C-12), 22.212 and 25.826 (C-7, C-8), 123.212 (C-3, C-5), 140.922 and 140.992 (C-2, C-6), 146.244, 146.315 and 146.502 (C-1) 3'P-NMR (500 MHz, D$_2$O)δ: −3.735 and -15.223 FAB-MS: [M+H]$^+$ 303.0730 M/Z, calculated for C$_{12}$H$_{17}$O$_4$PNa+H formula 303.0739

Example 5
Synthesis of di(propofol) phosphoric acid ester

Butyllithium (2.24 ml of 2.5M solution in hexanes; 5.6 mmol) was added dropwise to propofol (1.0 g, 5.6 mmol) in 10 ml of ether at −30° C. under nitrogen. The solute on was stirred at −30° C. for 30 min then allowed to warm to room temperature. To this solution was then added dropwise a solution of phosphorus oxychloride (0.444 g, 2.9 mmol) in 5 ml of ether at −30° C. The solution was allowed to warm to room temperature, then water (5 ml) was added and stirring was continued for 1 hr. Sodium hydroxide (20 ml of 1 M) and 20 ml of hexanes was added. The organic phase was washed with 1 M NaOH, water, then dried over sodium sulfate. The solvents were removed and the residue was dissolved in acetone (10 ml) and treated with 10 ml of 1 M NaOH and stirred for 2 hr. Most of the acetone was removed and the aqueous residue was adjusted to pH 5 with HCl, followed by extraction with hexanes. Evaporation of the hexanes left a white crystalline solid of di(propofol) phosphoric acid ester. The yield was 0.920 g (75%), mp 154° C.

The nuclear magnetic resonance spectra (proton and phosphorus) were consistent with structure: $^1$H-NMR (500 MHz, $CDCl_3$)δ: 1.036(d, 24H, J=6.6 Hz, tetra-i-Pr), 3.342 (m, 4H, J=6.6 Hz, $C_7$—H, $C_8$-H, $C_{7'}$—H, $C_{8'}$—H), 7.047 (d, 4H, J=7.5 Hz, $C_3$—H, $C_5$—H, $C_{3'}$—H, $C_{5'}$—H), 10.400 (broad, 1H, P—OH) $^{31}$P-NMR (500 MHz, $CDCl_3$)δ: −9.6994

Example 6

Synthesis of di(propofol) phosphate monosodium salt

A solution of di(propofol) phosphoric acid ester (300 mg, 0.7 mmol) in 5 ml of ethanol was neutralized to pH 7.4 with 0.7 ml of 1 M NaOH. After removal of the solvent under vacuum, the residue was dissolved in ether and again evaporated to yield di(propofol) phosphate disodium salt as a white solid, 300 mg, 100% yield.

The fast atom bombardment mass spectrum was consistent with structure: FAB-MS: $[M+H]^+$ 436.1977 M/Z, calculated for $C_{24}H_{34}O_4PNa+Na$ formula 436.1979

Example 7

In vitro hydrolysis of propofol esters in various media

General procedure: Propofol ester was dissolved in the test medium at room temperature, and samples were removed periodically for analysis. The samples were extracted with hexane, the extracts were evaporated to dryness, and the residues were taken up in methanol. Analysis was by HPLC using methanol solvent through an ODS column and UV detection at 260 nm.

The approximate half-life for the hydrolysis of propofol hemisuccinate to propofol in various media were as follows:

| Medium | Half-Life to Hydrolysis |
| --- | --- |
| water (PBS buffer pH 7.4) | 2 weeks |
| albumin | 6 days |
| human saliva | 4 days |
| human plasma | 3 days |
| human blood, whole | 2 days |
| rat blood, whole | 2 hrs |

The approximate half-life for the hydrolysis of (mono) propofol phosphate to propofol in human saliva was about four days.

Example 8

In vivo hydrolysis of propofol hemisuccinate

Propofol hemisuccinate sodium salt in aqueous solution was administered to adult male Sprague-Dawley rats by gavage. Blood was collected at 2, 4, 8 and 24 hours after dosing, and analyzed by HPLC as described in example 3.

Peak blood levels of propofol were seen at 2 to 4 hrs after dosing. At a dosage of 400 mg of propofol hemisuccinate per kg body weight, the blood level of propofol at 4 hrs was about 1 μg/ml. All the animals remained healthy and active through the two day observation period following the dosing.

Example 9

Effect of propofol esters on LDL-oxidation by copper, hydrogen Peroxide/horseradish Peroxidase and Myeloperoxidase The following experiment is based on the use of low density lipoprotein (LDL) as an oxidizable substrate. LDL is one of the plasma lipoproteins whose oxidation is thought to contribute to the pathogenesis of atherosclerosis. The copper-promoted, the hydrogen peroxide-/horseradish peroxidase-promoted and the myeloperoxidase-promoted oxidation of LDL are models for the free radical-induced oxidation of LDL that occurs in vivo.

LDL was isolated from heparinized plasma of normal human donors by ultracentrifugation. Most of the experiments described in this study were performed immediately after isolation. Examples and further details of the experimental procedures may be found in N. Santanam et al. *J. Clin Invest*. 95(6):2594 (1995) and *FEBS Leters*, 414:549–551 (1997).

The formation of conjugated dienes was measured in a spectrophotometer (model DB-3500; SLM-AMINCO, Urbana, Ill.) equipped with a 12 position sample changer. Samples and references were measured continuously for periods of up to several hours. Typically, 100 μg/ml of LDL was incubated in PBS with 1 U horseradish peroxidase (type X, 260 U/mg) in the presence of 50 μM $H_2O_2$. For copper-mediated oxidation, 100 μg/ml LDL was incubated with 5 μM copper sulfate solution.

The copper-promoted oxidation of LDL was not significantly affected by the presence of the propofol pro-drugs (propofol phosphate, dipropofol phosphate, propofol hemisuccinate) at concentrations of 5 μM. However, in the presence of 5 μM propofol, the oxidation was almost totally inhibited.

The oxidation of LDL in the presence of horseradish peroxidase/hydrogen peroxide was not significantly affected by the presence of either di(propofol)phosphate (5 μM) or propofol monophosphate (5 μM). In the presence of propofol hemisuccinate (5 μM) the oxidation was slightly inhibited. In the presence of 5 μM propofol, the oxidation was almost totally inhibited.

The oxidation of LDL in the presence of myeloperoxidase was partly inhibited in the presence of propofol hemisuccinate.

Human low density lipoprotein (huLDL) in the presence of myeloperoxidase undergoes oxidative modification. The oxidative damage may be measured by spectrophotometric detection of the resulting conjugated dienes (N. Santanam & S. Parthasarathy, *J. Clin. Invest*, 95(6):2594 (1995)). Following the procedures of Santanam et al., it was observed that the myeloperoxidase-mediated oxidation of huLDL was significantly inhibited in the presence of added propofol hemisuccinate.

The present invention provides water soluble esters of 2,6-diisopropylphenol and methods of using these compounds. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. Applicants do not admit by their citation of various references in this document that any particular reference is "prior art" to their invention.

What is claimed is:

1. A pharmaceutical composition comprising a pharmaceutically acceptable carrier and a pharmacologically effective amount of a compound having the structure:

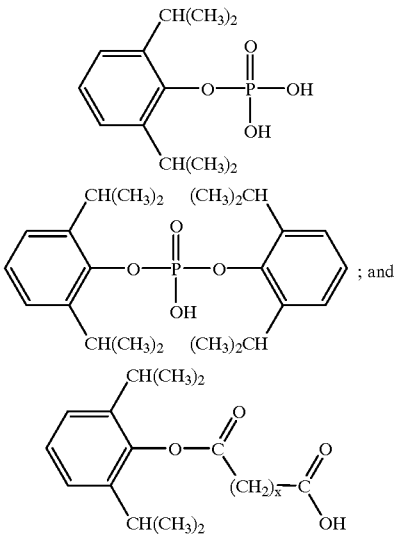

or a pharmaceutically acceptable salt of any of the foregoing, wherein X is 2, 3 or 4.

2. The pharmaceutical composition of claim 1 wherein the pharmaceutically acceptable carrier is an aqueous solution.

3. The pharmaceutical composition of claim 1 wherein the pharmaceutically acceptable carrier comprises a transdermal delivery vehicle.

4. The pharmaceutical composition of claim 1 in the form of an injectable solution.

5. The pharmaceutical composition of claim 1 contained in an aerosolizer or inhaler.

6. The pharmaceutical composition of claim 1 contained in a transdermal delivery system.

7. The pharmaceutical composition of claim 1 contained in a unit dosage form.

8. The pharmaceutical composition of claim 2 wherein the pharmaceutically acceptable carrier contains a detergent, an emulsifier or liposomes.

9. The pharmaceutical composition of claim 4 wherein the concentration of the compound in the injectable solution is between about 1 mg/ml to about 100 mg/ml.

10. The pharmaceutical composition of claim 7 wherein the unit dosage form contains about 100 mg to about 1 gm of the compound.

11. A method for inhibiting oxidation of biological material comprising contacting the material with an effective amount of a compound having a structure which is a member selected from the group consisting of:

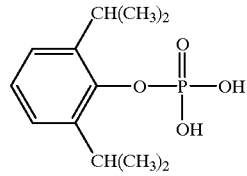

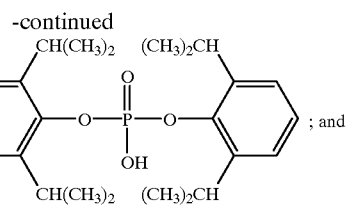

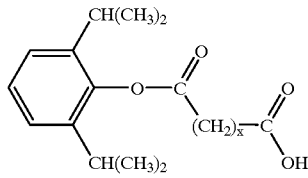

wherein X is 2, 3 or 4,
or a pharmaceutically acceptable salt of any of the foregoing.

12. The method of claim 11 wherein the effective concentration is about 10 μm to about 1 mM.

13. A method for the treatment of a pathologic condition having an inflammatory component in a subject comprising administering to the subject a pharmacologically effective amount of a compound having a structure which is a member selected from the group consisting of:

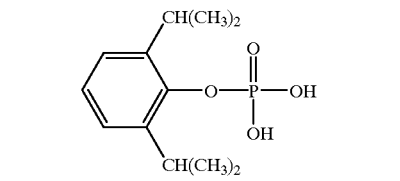

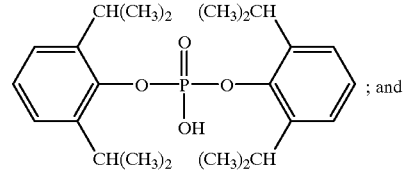

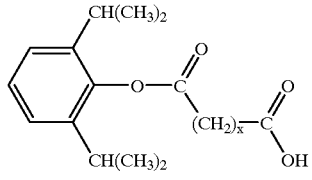

wherein X is 2, 3 or 4,
or a pharmaceutically acceptable salt of any of the foregoing.

14. The method of claim 13 wherein the effective amount is about 50 mg to about 2 g.

15. The method of claim 13 wherein the pathologic condition is arthritis.

16. The method of claim 13 wherein the pathologic condition is a pathologic condition of the nervous system.

17. The method of claim 16 wherein the pathologic condition is a neurodegenerative disease.

18. The method of claim 16 wherein the pathologic condition is trauma to the central nervous system.

19. The method of claim 17 wherein the neurodegenerative disease is a member selected from the group consisting of Friedrich's disease, Parkinson's disease, Alzheimer's disease, Huntington's disease, Pick disease, amyotrophic lateral sclerosis and multiple sclerosis.

20. The method of claim 18 wherein the trauma is spinal cord injury.

21. A method for the treatment of a pathologic respiratory condition in a subject comprising administering to the subject a pharmacologically effective amount of a compound having a structure which is a member of the group consisting of:

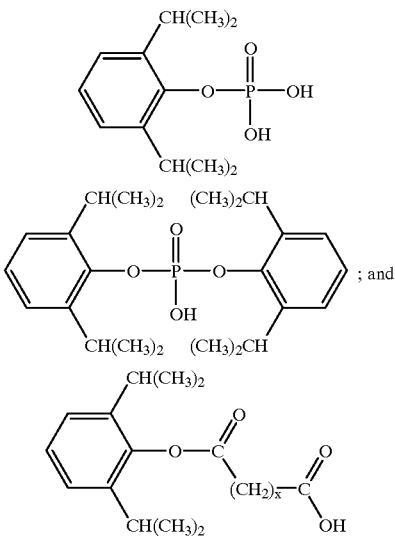

wherein X is 2, 3 or 4,
or a pharmaceutically acceptable salt of any of the foregoing.

22. The method of claim 21 wherein the effective dosage is about 0.1 mg to 10 mg/inhalation, 50 mg to 2 g orally/day.

23. The method of claim 21 wherein the pathologic respiratory condition is a member selected from the group consisting of acid aspiration, adult/infant respiratory distress syndrome, airway obstructive disease, asthma, bronchiolitis, bronchopulmonary dysplasia, cancer, chronic obstructive pulmonary disease, cystic fibrosis, emphysema, HIV-associated lung disease, idiopathic pulmonary fibrosis, immune-complex-mediated lung injury, exposure to an oxidizing agent, ischemia-reperfiision injury, mineral dust pneumoconiosis, drug-induced lung disease and silo-filler's disease.

24. The method of claim 21 wherein the respiratory disease is asthma.

25. The method of claim 21 wherein the compound is administered by inhalation as an aerosol, mist or powder.

26. The method of claim 25 wherein the aerosol, mist or powder delivers between about 1 mg and 50 mg per inhalation.

27. The method of claim 21 wherein the respiratory disease is a member selected from the group consisting of exposure to dust, ozone, hyperoxia, air pollution, diesel exhaust, nitric oxide, nitrogen dioxide, sulfur dioxide, tobacco smoke or other combustion byproducts.

28. A method for inducing anesthesia in a subject comprising administering to the subject a pharmacologically effective amount of a compound having a structure which is a member selected from the group consisting of:

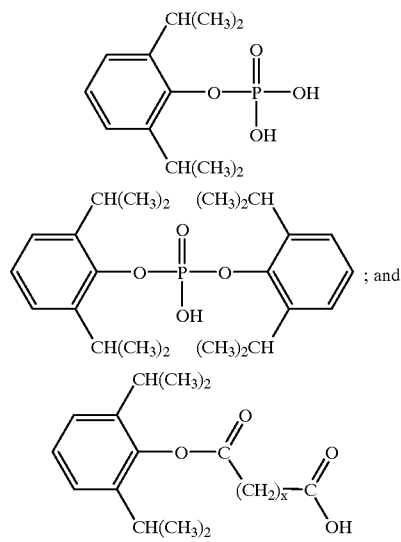

wherein X is 2, 3 or 4,
or a pharmaceutically acceptable salt of any of the foregoing.

29. The method of claim 28 wherein the effective amount is about 100 mg to about 1 g or by inhalation.

30. The method of claim 28 wherein the compound is administered in the form of an intravenous injection of an aqueous composition comprising the compound.

31. The method of claim 28 wherein the compound is administered by inhalation.

32. A method for inhibiting nausea and vomiting in a subject comprising administering to the subject a pharmacologically effective amount of a compound having a structure which is a member selected from the group consisting of:

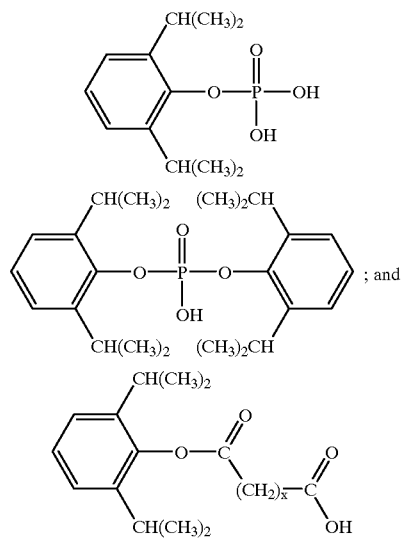

wherein X is 2, 3 or 4,
or a pharmaceutically acceptable salt of any of the foregoing.

33. The method of claim 32 wherein the effective amount is about 100 mg to about 1 g.

34. A method for the treatment of epileptic or convulsive disorders in a sbibject comprising administering to the subject a pharmacologically effective amount of a compound having a structure which is a member selected from the group consisting of:

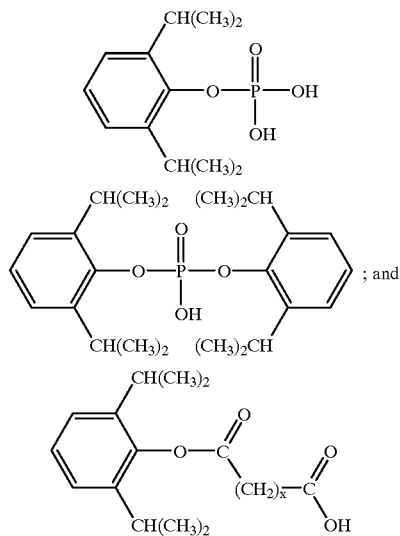

wherein X is 2, 3 or 4,
or a pharmaceutically acceptable salt of any of the foregoing.

35. The method of claim 34 wherein the effective dosage is about 100 mg to about 2 g.

36. A method for the treatment of pruritus in a subject comprising administering to the subject a pharmacologically effective amount of a compound having a structure which is a member selected from the group consisting of:

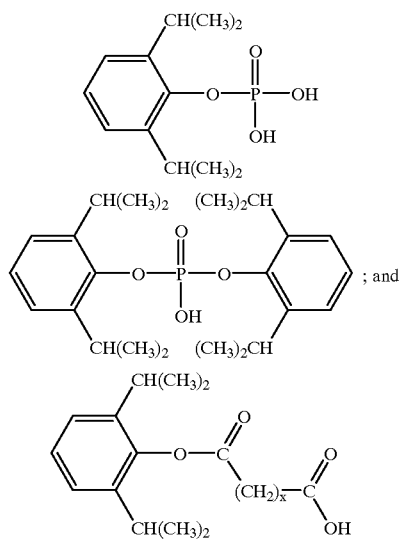

wherein X is 2, 3 or 4,
or a pharmaceutically acceptable salt of any of the foregoing.

37. The method of claim 36 wherein the effective amount is about 100 mg to about 1 g orally or about 0.01 mg/cm² to 5 mg/cm² topically.

38. A method for the treatment of a cancer in a subject comprising administering to the subject a chemotherapeutic agent and a pharmacologically effective amount of a compound having a structure which is a member selected from the group consisting of:

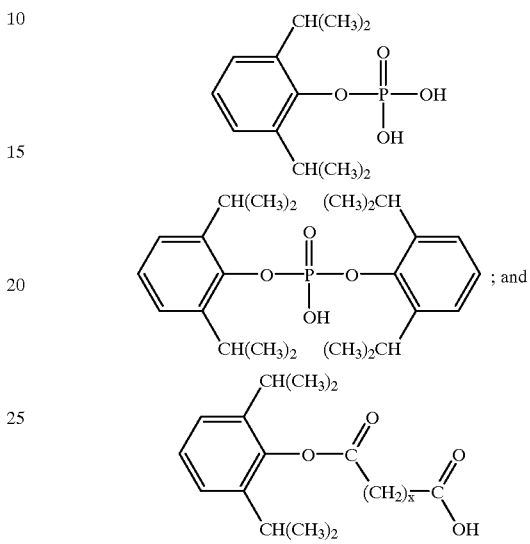

wherein X is 2, 3 or 4,
or a pharmaceutically acceptable salt of any of the foregoing.

39. The method of claim 38 wherein the effective amount is about 100 mg to about 1 g.

40. The method of claim 38 wherein the chemotherapeutic agent is 5-fluorouracil or doxorubicin.

41. The method of claim 38 wherein the cancer is colorectal cancer.

42. The method of claim 38 wherein the chemotherapeutic agent has activity as an oxidizing agent.

43. The method of claim 42 wherein the chemotherapeutic agent is bleomycin, doxorubicin or cisplatin.

44. A method for the treatment of a pathologic condition of the nervous system having an inflammatory component in a subject comprising administering to the subject a pharmacologically effective amount of propofol.

45. The method of claim 44 wherein the pathologic condition is a neurodegenerative disease.

46. The method of claim 44 wherein the pathologic condition is trauma to the central nervous system.

47. The method of claim 45 wherein the neurodegenerative disease is Friedrich's disease, Parkinson's disease, Alzheimer's disease, Huntington's disease, Pick disease, amyotrophic lateral sclerosis or multiple sclerosis.

48. The method of claim 46 wherein the trauma is spinal cord injury.

* * * * *

UNITED STATES PATENT AND TRADEMARK OFFICE
CERTIFICATE OF CORRECTION

PATENT NO.     : 6,254,853 B1                                              Page 1 of 1
DATED          : July 3, 2001
INVENTOR(S)    : Sheldon S. Hendler et al.

It is certified that error appears in the above-identified patent and that said Letters Patent is hereby corrected as shown below:

<u>Column 19,</u>
Line 47, replace "reperfiision" with -- reperfusion --

Signed and Sealed this

Thirtieth Day of March, 2004

JON W. DUDAS
*Acting Director of the United States Patent and Trademark Office*